US00PP10765P

United States Patent [19]

Didden

[11] Patent Number: Plant 10,765

[45] Date of Patent: Jan. 26, 1999

[54] POINSETTIA PLANT NAMED 'SALMONSTAR'

[75] Inventor: Frans Didden, Boskoop, Netherlands

[73] Assignee: Koninklijke Handelskwekerij Weduwe, P. Eveleens, & Zonen B.V., 'Royal Eveleens', Aalsmeer, Netherlands

[21] Appl. No.: 845,838

[22] Filed: Apr. 28, 1997

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

| | | | |
|---|---|---|---|
| P.P. 8,259 | 6/1993 | Jacobsen | Plt./86.4 |
| P.P. 9,347 | 10/1995 | Zerr | Plt./86.4 |
| P.P. 9,371 | 11/1995 | Zerr | Plt./86.4 |
| P.P. 9,474 | 3/1996 | Dahlqvist-Olsson | Plt./86.4 |

*Primary Examiner*—James R. Feyrer
*Attorney, Agent, or Firm*—C. A. Whealy

[57] ABSTRACT

A new and distinct cultivar of Poinsettia plant named 'Salmonstar', characterized by its dark salmon-colored bracts; bracts held horizontal to upright; compact and uniform growth habit requiring few plant growth retardant applications; freely branching; and very good postproduction longevity.

3 Drawing Sheets

The present invention relates to a new and distinct cultivar of Poinsettia plant, botanically known as *Euphorbia pulcherrima* Willd., hereinafter referred to by the cultivar name Salmonstar.

The new cultivar is a product of a mutation induction breeding program conducted by the inventor in Aalsmeer, The Netherlands. The objective of the breeding program was to develop compact poinsettia varieties that require little to no growth retardants and are suitable for smaller containers; that flower early; and have desirable bract and foliage color.

The new cultivar is an induced mutation of the commercial cultivar Peterstar, disclosed in U.S. Plant Pat. No. 8,259. The new cultivar originated by exposing unrooted cuttings of the cultivar Peterstar to gamma radiation at a level of 2,500 rads eight times for a period of 15 minutes each. Following the radiation treatments, the cuttings were rooted and terminal apices were removed to promote lateral branch development. After lateral branches from the pinching reached sufficient size, terminal cuttings were harvested, planted and flowered in Aalsmeer, The Netherlands. The cultivar Salmonstar was discovered and selected by the inventor as a single flowering plant within this population in December, 1993. The selection of this plant was based on its desirable bract color.

Asexual reproduction of the new cultivar by terminal cuttings taken at Aalsmeer, The Netherlands, has shown that the unique features of this new Poinsettia are stable and reproduced true to type in successive generations of asexual reproduction.

The following traits have been repeatedly observed and are determined to be the unique characteristics of 'Salmonstar'. These characteristics in combination distinguish 'Salmonstar' as a new and distinct cultivar:

1. Distinct dark salmon-colored bracts.
2. Bracts held horizontal to upright.
3. Compact and uniform growth habit requiring few plant growth retardant applications.
4. Freely branching.
5. Very good postproduction longevity.

The new cultivar differs primarily from the parent cultivar Peterstar in its distinct dark salmon bract color. Additionally in side-by-side comparisons conducted by the inventor in Aalsmeer, The Netherlands, the new cultivar differs from plants of the cultivar Peterstar in the following characteristics:

1. Plants of the new Poinsettia are not as freely branching as plants of the cultivar Peterstar.
2. Leaves of the new Poinsettia are broader than leaves of the cultivar Peterstar.
3. The vein color on the lower surface of leaves of the new Poinsettia is greenish whereas the vein color on the lower surface of leaves of the cultivar Peterstar is reddish.
4. Plants of the new Poinsettia have longer leaf petioles than plants of the cultivar Peterstar.

The new cultivar can be compared to the Poinsettia Nobelstar, disclosed in U.S. Plant Pat. No. 9,474. However in side-by-side comparisons conducted by the inventor in Aalsmeer, The Netherlands, plants of the new cultivar differs from plants of the cultivar Nobelstar in the following characteristics:

1. The upper surface of bracts of the new Poinsettia is lighter in color than the upper surface of bracts of the cultivar Nobelstar.
2. Nectaries of cyathia of the new Poinsettia are smaller than nectaries of the cultivar Nobelstar.
3. The nectaries of cyathia of the new Poinsettia have a distinct red margin whereas nectaries of the cultivar Nobelstar have a less noticeable red margin.
4. The upper petiole surfaces of the new Poinsettia are more red than petiole surfaces of the cultivar Nobelstar.
5. Cyathia of the new Poinsettia open earlier than cyathia of the cultivar Nobelstar.

The accompanying colored photographs illustrate the overall appearance of the new cultivar, showing the colors as true as it is reasonably possible to obtain in colored reproductions of this type.

The first photograph comprises a top perspective view of a typical potted plant of 'Salmonstar'.

The second photograph comprises a close-up view of a typical inflorescence of 'Salmonstar'.

The third photograph comprises a top perspective view of upper (left) and lower (right) surfaces of typical leaves (top) and bracts (bottom) of 'Salmonstar'. Flower bract and foliage colors in the photographs may appear different from the actual colors due to light reflectance.

The cultivar Salmonstar has not been observed under all possible environmental conditions. The phenotype may vary somewhat with variations in environment such as temperature, daylength and light intensity, without, however, any variance in genotype. The following observations, measurements and comparisons describe plants grown in Aalsmeer, The Netherlands, under commercial practice in a glass-covered greenhouse with temperatures of 20° to 21° C. initially, then decreasing to 14° C. as plants matured to improve the postproduction longevity. Short day treatments of 14 hours of dark were initiated two weeks after pinching to initiate flowering.

In the following description, color references are made to The Royal Horticultural Society Colour Chart except where general terms of ordinary dictionary significance are used.

Classification:

*Botanical.*—*Euphorbia pulcherrima* Willd.

*Commercial.*—Poinsettia.

*Cultivar.*—'Salmonstar'.

Parentage: Induced mutation of Poinsettia cultivar Peterstar disclosed in U.S. Plant Pat. No. 8,259.

Propagation:

*Type cutting.*—Terminal cuttings.

*Time to initiate roots.*—7 to 10 days at 21C.

*Rooting habit.*—Fine, freely branching.

Plant description:

*Plant form.*—Inverted triangle, top of plant rounded to flat.

*Growth habit.*—Freely branching and upright. Branching is enhanced by the removal of the apical shoot tip. Moderate growth rate and moderate vigor. Relatively compact, best suited for 12.5 to 15-cm containers.

*Plant height.*—20 to 25 cm.

*Stem description.*—Diameter: 5 to 7 mm. Internode length: 1.5 to 3 cm. Color: Green and red.

*Foliage description.*—Arrangement: Opposite. Size: Length: 9 to 12 cm. Width: 5 to 7.5 cm. Petiole length: 4 to 6 cm. Shape: Broadly ovate. Tip: Acute. Base: Cuneate. Margin: Entire to weakly lobed. Texture: Leathery. Color: Mature foliage upper surface: 137B. Mature foliage lower surface: 137C. Venation, upper surface: Green and red. Venation, lower surface: Green. Petiole: Red.

Inflorescence/flower description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under short day/long night conditions.

*Time to flower.*—About 9 weeks under short day/long night conditions.

*Inflorescence size.*—Diameter: About 24 cm. Height (depth): 2 to 3 cm.

*Flower bracts.*—Attitude: Horizontal to upright, about 45° to stem axis. Quantity of flower bracts: 7 to 9 fully colored bracts per inflorescence, usually 1 to 3 green and red transitional bracts. Size: Length: 11 to 13 cm with petiole. Width: 6 to 7.5 cm. Shape: Broadly elliptic. Tip: Acute. Base: Cuneate. Margin: Entire. Texture: Weakly or not rugose between veins, smooth. Color: Mature, upper surface: 44D/50A. Mature, lower surface: 43D/44D. Venation, upper surface: Darker than 44D/50A. Venation, lower surface: Green to slightly red.

*Cyathia.*—Quantity: About 9 per inflorescence. Diameter of cyathia cluster: About 2 cm. Nectaries: Usually one and sometimes two per cyathium. Size: 3 to 6 mm. Color: Yellow or orange with red margin.

Disease resistance: No fungal, bacterial nor viral problems observed.

Postproduction longevity: Generally more than 3.5 weeks under interior conditions.

It is claimed:

1. A new and distinct cultivar of Poinsettia plant named 'Salmonstar', as illustrated and described.

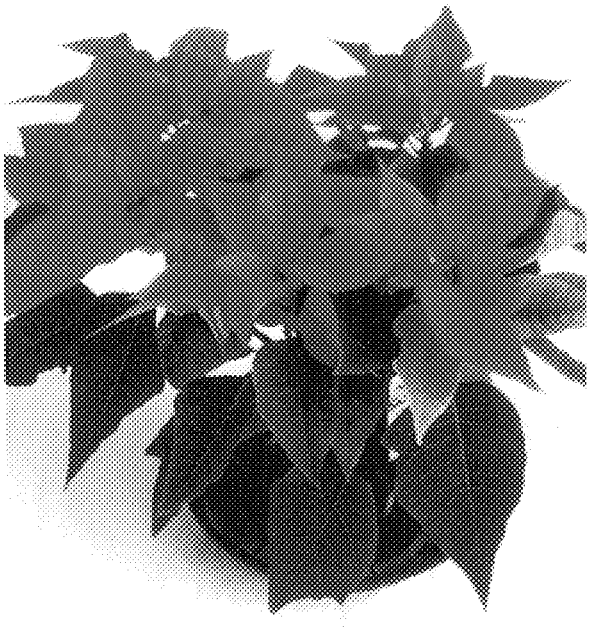

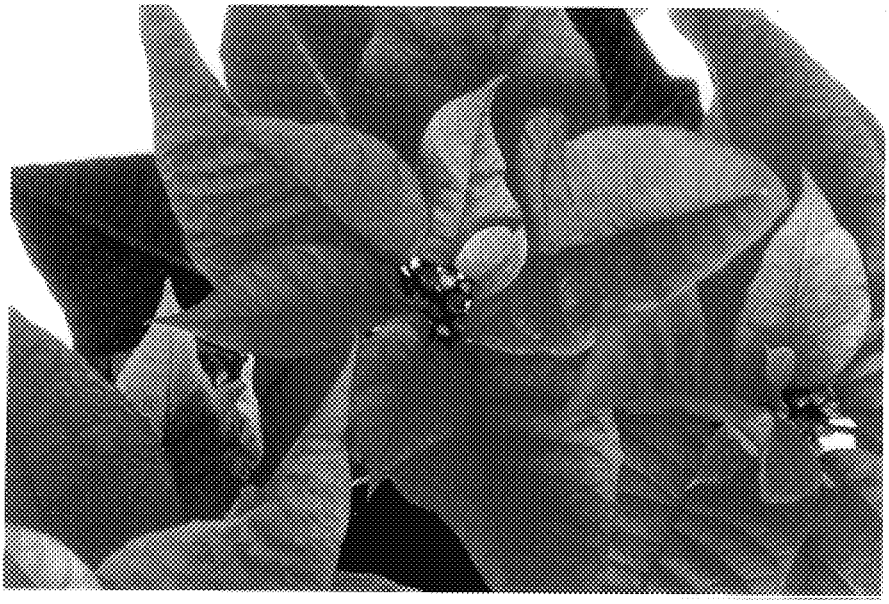

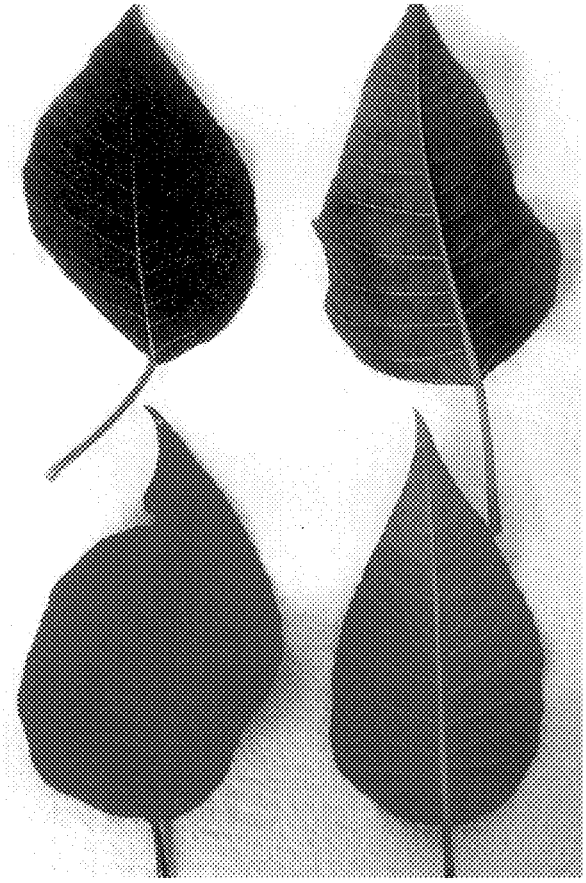

* * * * *